United States Patent [19]

Kapmeyer

[11] Patent Number: 5,183,766
[45] Date of Patent: Feb. 2, 1993

[54] DISPERSION POLYMERS, PROCESSES FOR THEIR PREPARATION AND THEIR USE

[75] Inventor: Wolfgang Kapmeyer, Marburg, Fed. Rep. of Germany

[73] Assignee: Behringwerke Aktiengesellschaft, Marburg, Fed. Rep. of Germany

[21] Appl. No.: 542,049

[22] Filed: Jun. 22, 1990

Related U.S. Application Data

[62] Division of Ser. No. 39,107, Apr. 16, 1987, Pat. No. 4,962,046.

[30] Foreign Application Priority Data

Apr. 18, 1986 [DE] Fed. Rep. of Germany ....... 3613111

[51] Int. Cl.$^5$ ..................... G01N 33/546; C12Q 1/00
[52] U.S. Cl. .................... 436/533; 524/812; 436/534; 435/7.1; 435/7.92
[58] Field of Search ............. 524/812; 526/304; 436/531–534; 435/7.1, 7.92

[56] References Cited

U.S. PATENT DOCUMENTS

| | | | |
|---|---|---|---|
| 4,118,349 | 10/1978 | Bonacker et al. | 436/533 |
| 4,224,304 | 9/1980 | Sawai et al. | 436/533 |
| 4,336,177 | 6/1982 | Backhouse et al. | 524/458 |
| 4,337,189 | 6/1982 | Bromley et al. | 524/458 |
| 4,419,465 | 12/1983 | Backhouse et al. | 524/523 |
| 4,427,836 | 1/1984 | Kowalski et al. | 523/201 |
| 4,563,431 | 1/1986 | Pauly et al. | 436/533 |
| 4,690,906 | 9/1987 | Duheille et al. | 436/533 |
| 4,962,046 | 10/1990 | Kapmeyer | 436/533 |

Primary Examiner—James C. Housel
Assistant Examiner—William Ky Chan
Attorney, Agent, or Firm—Finnegan, Henderson, Farabow, Garrett and Dunner

[57] ABSTRACT

Dispersion polymers, processes for their preparation and their use are disclosed. The dispersion polymers being obtained by a seed polymerization process in the presence of seed latices with a high residual monomer content and a monomer mixture of at least one compound of the formula I

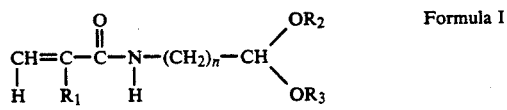

wherein
n = 1−6;
$R_1$ = H or $CH_3$ and
$R_2$ and $R_3$ are identical or different, where $R_2$ and $R_3$ = —$(CH_2)_m$—$CH_3$, and m = 0−7, or

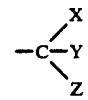

in which X, Y and Z = $(CH_2)_p$—$CH_3$ and p = 1−3, where X, Y and Z are identical or different,
or $R_2$ and $R_3$ = an aryl radical,
and if appropriate acrylic acid, methacrylic acid, crotonic acid and monomers from which the seed latex is prepared. The invention furthermore relates to the biologically active latex conjugates which are obtained using the dispersion polymers and are particularly suitable for serological and immunological determination methods.

16 Claims, 2 Drawing Sheets

DISPERSION POLYMERS, PROCESSES FOR THEIR PREPARATION AND THEIR USE

This is a division of application Ser. No. 07/039,107, filed Apr. 16, 1987, now U.S. Pat. No. 4,962,046.

The invention relates to dispersion polymers, processes for their preparation and their use, the dispersion polymers consisting of latex particles which have been prepared by a seed polymerization process by a procedure in which the seed polymer used still has a content of 5 to 50% by weight of monomers which have not polymerized completely and the seed polymerization is carried out with monomers, at least one monomer being a compound containing acetal groups.

Biologically active dispersion polymers are obtained therefrom by binding biologically active substances which have free amino groups to reactive groups derived from the aldehyde function which are present on the surface of the dispersion polymer particles according to the invention. These biologically active latex conjugates are suitable for serological or immunological determination methods.

It is known that the sensitivity of serological or immunological determination methods can be increased by using indicator or carrier particles charged with the corresponding immunological reagent. Examples of carriers which can be used are red blood corpuscles or cells of a cell culture. Latex particles with a diameter of 0.02 to 5 pm are also used for this purpose.

Latex particles which contain acetal functions bonded via acid amide groups are known from European Patent Application EP-A 82110273.8. Latex cores previously prepared in an aqueous medium are swollen with vinyl monomers containing acetal functions bonded via acid amide groups, and these vinyl monomers, which must be sufficiently waterinsoluble, are then copolymerized together with other monomers, which may be hydrophilic or ionic in nature. Such reagents can be used for the nephelometric and turbidimetric determination of proteins.

For this purpose, antibodies against the protein to be determined are bonded to the latex. After appropriate dilution of the latex charged with antibodies, the reagent thus formed can be used for measurement: after incubation with the antigen to be determined, agglutinates which can be measured nephelometrically or turbidimetrically are formed. The resulting scattered light signals according to this prior art are quite low and therefore do not allow a readily reproducible measurement. An increase in the detection sensitivity of the reagent and also an associated increase in the scattered light signals during the reaction between a reagent according to the prior art and the antigen to be detected cannot be achieved easily.

It has now been found, surprisingly, that the disadvantages described for the prior art can be overcome by using carrier particles which are prepared by a method which comprises using previously prepared latex cores which have not polymerized completely and which still contain a considerable proportion of the non-polymerized monomers employed, that is to say which have a high residual monomer content, and co-polymerizing these latex cores which have not polymerized completely and are thus swollen in the monomer, for example styrene, with acrylic or methacrylic monomers containing acetal groups bonded via acid amide groups, if appropriate together with acrylic or methacrylic acid monomers, in an aqueous medium.

The invention thus relates to dispersions which contain latex carrier particles which have been prepared by the seed dispersion process in which only 30-90% by weight, preferably 40-80% by weight, of the monomers present have polymerized completely in the seed latex used, and on the surface of which is a copolymer which has been polymerized from a monomer mixture which contains monomers of the formula I

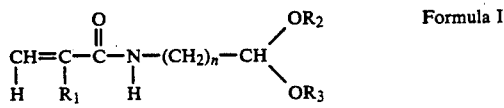

in which
n = 1 − 6;
$R_1$ = H or $CH_3$ and
$R_2$ and $R_3$ are identical or different, where
$R_2$ and $R_3$ = —$(CH_2)_m$—$CH_3$, and m = 0—7, or

in which X, Y and Z = $(CH_2)_p CH_3$ and p = 1 − 3,
where X, Y and Z are identical or different,
or $R_2$ and $R_3$ = an aryl radical,
and if appropriate crotonic and/or acrylic and/or methacrylic acid, and if appropriate the monomer from which the seed polymers are formed, that is to say, for example, styrene.

The invention furthermore relates to a process for the preparation of the dispersions, which comprises first preparing a latex dispersion seed by polymerizing monomers, such as, for example, styrene, such that only 30-90% by weight of the monomers employed have polymerized completely, and subsequently separating off the excess monomer which is not dissolved in the polymer by filtration or by extensive dialysis and then adding a monomer mixture and polymerizing this on. This mixture contains compounds with terminal acetals of the formula I and if appropriate crotonic and/or acrylic and/or methacrylic monomers, as well as monomers from which the seed polymer is formed, for example styrene. The seed latex is preferably polymerized by polymerizing only 40-80% (w:w) of the monomers present completely. A polymerization process for which 50-70% (w:w) of the monomers present have polymerized completely is preferred for the seed latex.

Polymer cores which still contain 5-50% by weight of monomer, based on the polymer, are thus obtained by the process according to the invention. Preparations which contain 10-40% by weight of monomer, based on the polymer, are preferred. Preparations which contain 20-30% by weight of monomer, based on the polymer, are particularly preferred.

The latex particles used as the seed dispersion for the dispersions according to the invention should be polymers which are not film-forming. By "not film-forming" there are understood polymer latex particles which do not form a film and do not coalesce under the use conditions. Polymers of carbocyclic aromatic monovinylidene monomers, such as styrene, vinyltoluene and vinylnaphthalene, and mixtures of these monomers with one another and/or with methyl methacrylate and acrylonitrile are preferred. Particularly preferred seed dispersions are polystyrene latices. A polystyrene seed dispersion is prepared by processes which are known per se.

To prepare the dispersion polymer according to the invention, about 20-80% (w:w) of the amount of an emulsifier which would be required for maximum monomolecular cover of the latex surface is in principle added to a previously prepared latex with a particle diameter of 0.02 to 2 μm, preferably 0.05 to 0.5 μm. Measurements for the determination of the amount of emulsifier which leads to maximum cover of the latex surface are carried out with the aid of a tensiometer. They have been published, for example, by I. Phrma and S.-R. Chen in Journal of Colloid and Interface Science, Volume 74 (1979), pages 90-102 and for the first time by S. H. Maron, M. E. Elder and I. N. Ulevitch in Journal of Colloid Interface Sciences, Volume 9 (1954), pages 89-104.

Examples of possible emulsifiers are polyglycol ethers with long-chain aliphatic alcohols which preferably contain 10-20 carbon atoms, or alkylphenol, the alkyl radical of which preferably contains 6-12 carbon atoms, or dialkylphenol or trialkylphenol, the alkyl radicals of which are preferably branched alkyl radicals with in each case 3-12 carbon atoms. Examples of these are reaction products of ethylene oxide with lauryl alcohol, stearyl alcohol, oleyl alcohol, coconut fatty alcohol, octylphenol, nonylphenol, diisopropylphenol, triisopropylphenol, di-t-butylphenol and tri-t-butylphenol. Reaction products of ethylene oxide with polypropylene glycol are also suitable.

Suitable ionic emulsifiers are above all anionic emulsifiers, in particular alkali metal or ammonium salts of alkylsulfonates or alkylarylsulfonates and of the corresponding sulfates, phosphates or phosphonates, which optionally contain oxyethylene units between the particular hydrocarbon radical and the anionic group. Examples of these are sodium dodecyl-sulfate, sodium lauryl-sulfate, sodium octylphenol glycol ether-sulfate, sodium dodecylbenzenesulfonate, sodium lauryl diglycol-sulfate, ammonium tri-t-butylphenol pentaglycol-sulfate and ammonium tri-tbutylphenol octaglycol-sulfate. Sodium dodecyl-sulfate is preferably employed.

A monomer mixture which contains at least one compound of the formula I containing acetal groups is added dropwise, with stirring, to the seed dispersion which, in addition to the emulsifier, contains a free radical starter (initiator). The temperature of the dispersion is between +10° C. and +120° C., preferably between +50° C. and +90° C.

The polymerization is carried out by processes which are known per se in the presence of an initiator which forms free radicals, for example a peroxide compound or an aliphatic azo compound. The initiator is water-soluble; it is employed in an amount of 0.05 to 10% by weight, preferably 0.1 to 3% by weight (based on the total amount of the monomers). Examples of known initiators which form free radicals are hydrogen peroxide, alkali metal or ammonium salts of peroxydisulfuric acid or peroxydiphosphoric acid, for example sodium peroxydisulfate, potassium peroxydisulfate and ammonium peroxydisulfate, and furthermore alkyl hydroeroxides, such as t-butyl hydroperoxide, dialkyl peroxides, such as di-t-butyl peroxide, diacyl peroxides, such as diacetyl peroxide, dilauroyl peroxide and dibenzoyl peroxide, as well as azodiisobutyronitrile, azodicarboxamide and azo-gamma,gamma'-bis(4-cyanovaleric acid). The alkali metal or ammonium salts of peroxydisulfuric acid, such as sodium, potassium and ammonium peroxydisulfate, are preferably employed.

If appropriate, the initiator is used together with a reducing agent, in particular with an alkali metal salt or alkaline earth metal salt of a reducing sulfur-containing acid; compounds which are preferably suitable are sulfites, bisulfites, pyrosulfites, dithionites, thiosulfates and formaldehyde-sulfoxylates. Glucose and ascorbic acid can also similarly be used.

The compounds of the formula I are used as monomers containing acetal groups, and an acryl- or methacrylamidoalkylaldehyde di-alkyl acetal where alkyl=$C_2$ to $C_8$ is preferably used. Acryl- or methacrylamidoacetaldehyde din-pentyl acetal is especially suitable.

Up to 30% by weight, based on the total mixture, of styrene, vinylnaphthalene or vinyltoluene can be added to the monomer mixture containing a compound of the formula I. If appropriate, the monomer mixture can also additionally contain up to 30% by weight, based on the total mixture, of methacrylic acid, acrylic acid or crotonic acid.

The monomer mixture is added to the seed dispersion in amounts of 90 to 5% by weight; preferably 40 to 10% by weight, based on the total amount of the seed dispersion and monomer mixture.

It may be important for successful polymerization in the presence of the seed polymer for the monomer mixture to be added dropwise with continuous stirring to the suspension of the latex cores under polymerization conditions, that is to say at a temperature of +10° C. to +120° C., preferably +50° C. to +90° C. During the dropwise addition, the amount of monomers added is continuously attracted to the already finished seed latex particles and is polymerized onto these to form further polymer around the latex particle.

The polymer is then freed from excess monomers, residues of the initiator and the emulsifier by known processes. The polymer is advantageously subjected to dialysis, for example against $NaHCO_3$ buffer (0.01 to 0.05% by weight).

To prepare the biologically active dispersions according to the invention, also called latex conjugates below, a suspension of the latex particles polymerized by seed polymerization in the manner described above is brought to a pH of less than 5, preferably less than 3, and incubated with the immunologically active material to be bound, such as, for example, antibodies, antigens or haptens.

The unstable bonds between an amino group of the protein and the aldehyde liberated on the latex particle according to the invention are reduced by known processes. A solution of sodium cyanoborohydride in neutral buffer is preferably used for this. Any non-bound immunologically active material or other impurities are removed from the reaction mixture. This is advantageously effected by centrifugation or washing on suitable membranes.

The seed-polymerized latices according to the invention are distinguished by a particularly high stability. They are suitable for the preparation of sensitive reagents. The reagents according to the invention can be dried by lyophilization.

Figure 1:
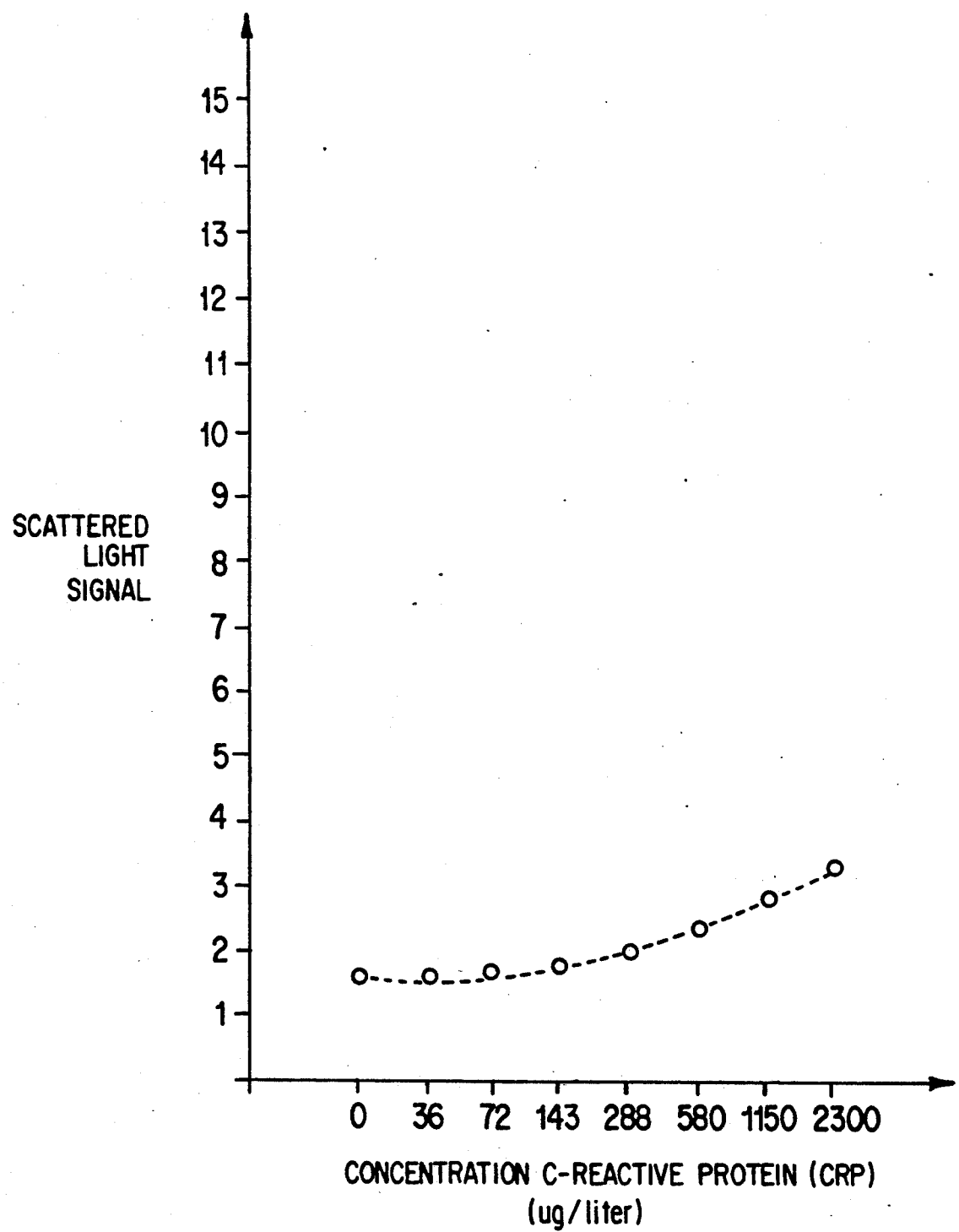
FIG. 1 shows nephelometric measurement as in the prior art

Reagents prepared according to the prior art show, on nephelometric or turbidimetric measurement, a reaction with the antigen to be detected, with agglutination and thus an increase in the scattered light signal or the extinction in the measurement cell. Thus, for example, a reagent for the determination of C-reactive protein, an important inflammation parameter, has been prepared using rabbit antibodies against C-reactive protein (CRP). If this reagent is reacted with different CRP concentrations and the scattered light signals are measured in a nephelometer after an incubation time of 30 minutes, a standard curve which shows higher scattered light signals as the CRP concentration increases is obtained. Such a standard curve is shown in FIG. 1. It can be clearly seen that only low scattered light signals can be measured for the CRP concentrations employed. Associated with this is a low sensitivity of the measurement, the lower detection limit of the reagent being about 288 μg/liter CRP; that is to say CRP concentrations in the range between 36 μg/liter and 288 μg/liter can not be detected.

Figure 2:
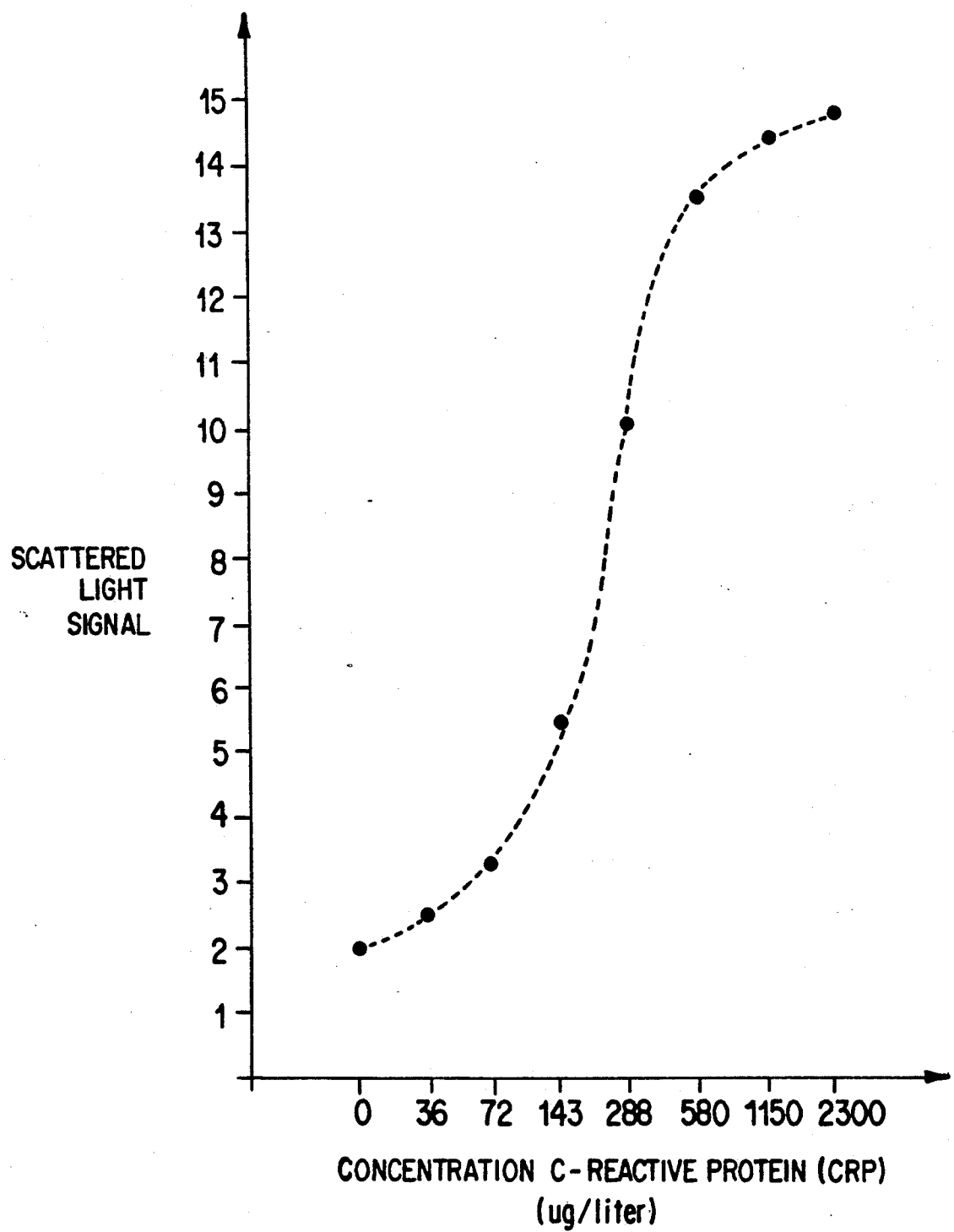
FIG. 2 shows nephelometric measurement according to the presentation.

The reagent according to the invention, prepared by binding antibodies, for example against CRP, to latex preparations obtained by seed polymerization on polymers which contain residual monomers and have not polymerized completely exhibits, on the other hand, a much stronger agglutination reaction after reaction with CRP. If this reagent according to the invention is reacted with different CRP concentrations and the scattered light signals are measured in a nephelometer after an incubation time of 30 minutes, a standard curve which already shows high scattered light signals at low CRP concentrations is obtained. Such a standard curve is shown in FIG. 2. It can be seen that the sensitivity of the reagent is so high that even low CRP concentrations down to 36 μg/liter can be measured. Furthermore, the scattered light signals for CRP concentrations of between 36 and 2,300 μg/liter are very much higher than for a reagent according to the prior art. This means that the reproducibility of the measurement is very much better than that according to the prior art.

Other reagents according to the invention with corresponding advantageous properties are obtained if the latex preparations according to the invention are charged, for example, with antibodies against alpha-fetoprotein (AFP), ferritin, human placental lactogen (HPL), thyroxin-binding globulin (TBG), immunoglobulin E, $\beta_2$-microglobulin, pregnancy-specific $\beta_1$-glycoprotein and human chorionic gonadotropin (μHCG).

Monoclonal antibodies can also advantageously be used for the preparation of the reagents according to the invention. Latex preparations can similarly be charged with bacterial or viral proteins, such as, for example, streptolysin 0, streptococcus B antigen, H. influenza antigen, pneumococcus antigen, lues antigen, toxoplasma antigen, HBsAg, rubella antigen, herpes antigen and tetanus antigen, and the corresponding antibodies can be detected by these antigencharged reagents according to the invention.

Finally, latex preparations according to the invention can be charged in the same manner with derivatized haptens, for example hormones or medicaments, such as thyroxin ($T_4$), triiodothyronine ($T_3$), cortisol, progesterone, testosterone, gentamycin and digoxin, giving biologically active dispersion polymers. The reagents according to the invention, with which the concentration of the haptens mentioned can be measured are used by inhibition tests, that is to say by simultaneous use of suitable antibodies.

The latex preparations according to the invention are easy to prepare and to link with sensitive immunologically active materials under gentle conditions to give a diagnostic reagent.

The latex conjugates can be used in all diagnostic methods which measure changes in particle size, for example in qualitative and semi-quantitative determinations of substances with the aid of visual latex agglutination tests and in nephelometric or turbidimetric determinations of trace proteins in the direct or competitive agglutination test or in the latex-hapten inhibition test.

EXAMPLES

1. Preparation of the seed polymer 310 ml of doubly-distilled water saturated with nitrogen were introduced into a cylindrical glass vessel equipped with a gas inlet and gas outlet tube and a magnetic stirring rod. 500 mg of sodium stearate were added and were dissolved by stirring. 1.5 ml of 25% strength ammonia were also added. The pH was checked and was 11.09. The polymerization vessel was freed from oxygen by evacuating and filling with nitrogen several times. The detergent solution was warmed to +70° C. with the aid of a waterbath, while stirring continuously. 90 ml of freshly distilled styrene were then introduced under nitrogen with the aid of a dropping funnel with pressure compensation into the polymerization vessel. The mixture was stirred at +70° C. for 15 minutes to emulsify the styrene. The temperature was then raised to +90° C. and the mixture was stirred for a further hour. 67.5 mg of potassium peroxydisulfate, dissolved in 50 ml of distilled water saturated with nitrogen, were then added. The mixture was stirred at 90° C. for 80 minutes. The polystyrene was added through a folded filter. Under certain circumstances, a few ml of styrene remain on the filter during this operation. This styrene could not be dissolved completely in the polystyrene, because some excess of styrene was present.

The filtered polystyrene was dialyzed against 10 liters of 0.01% (w:w) strength ammonium bicarbonate solution (with 0.01% (w:w) of $NH_4HCO_3$; 0.01% by weight of $NaN_3$; brought to pH 10.0 with 10.5 ml of 25% strength by weight ammonia in 10 liters) for 50 hours. After the dialysis, 410 ml of polymer with a dry weight of 12.8 g/dl were obtained. About 60% of the monomer employed had thus been polymerized. It was possible to increase the content of the polymerized styrene by increasing the polymerization time by 5 to 10 minutes, the monomer dissolved in the polystyrene being simultaneously reduced.

On the other hand, it was possible to reduce the content of styrene which had polymerized completely by reducing the polymerization time by 5 to 10 minutes, the monomer dissolved in the styrene being simultaneously increased.

2. Seed polymerization using the polymer prepared according to Example 1.

156.3 ml of a polystyrene latex dispersion with a solids content of 12.8% by weight, 238.7 ml of distilled water and 250 mg of sodium dodecyl-sulfate were introduced into a cylindrical glass vessel equipped with a gas inlet and gas outlet tube and a magnetic stirring rod and were dissolved by stirring. The polymerization vessel was freed from oxygen by evacuating and filling with nitrogen several times. The latex detergent mixture was heated to +70° C. in a waterbath, while stirring continuously.

A monomer mixture prepared from 2 ml of styrene, 2 ml of methacrylamidoacetaldehyde di-n-pentyl acetal and 1 ml of methacrylic acid was added under nitrogen. The mixture was then emulsified at about 20° C. for 1 hour, while stirring.

The polymerization batch was then warmed to +70° C. in a waterbath. After being stirred at +70° C. for 15 minutes, the copolymerization was started. For this, 5 ml of a potassium peroxydisulfate solution (16 mg/ml in distilled water) were added. The temperature of the polymerization batch was kept at +70° C. The mixture was stirred at the above temperature for 5 hours. The polymerization was thus ended and the dispersion was cooled to room temperature and filtered through a folded filter. 395 ml of a latex suspension were obtained. This was then dialyzed against an NaHCO$_3$ buffer solution (0.25 g/liter, pH 8-8.2) for 17 hours. 415 ml of a latex dispersion with a solids content of 6.8% by weight were obtained.

3. Binding of anti-CRP antibodies to a polymer according to the invention

Anti-CRP antibodies were bound to a polymer prepared according to Example 2. The polymer used was diluted to a solids content of 5.8% by weight with distilled water. An antiserum obtained by immunization of rabbits with purified CRP was isolated as the gamma-fraction by known methods. It was then concentrated until a protein content of 10 mg/ml was reached. 0.5 ml of the abovementioned polymer was mixed with 0.05 ml of the anti-CRP antibody solution. 0.025 ml of a 20% strength aqueous solution of eicosaoxyethylene sorbitan laurate (Tween ® 20) was then added and all the components were mixed again. 0.01 ml of 1 N HCl was added to this, so that the pH value reached about 2. After an incubation time of 30 minutes at room temperature, 0.125 ml of saturated aqueous sodium hydrogen phosphate solution (pH 6.5) and 0.125 ml of aqueous sodium cyanoborohydride solution (25 mg/ml) were added and the components were mixed thoroughly. The mixture was then incubated at room temperature for one hour.

This preparation was then centrifuged at about 50,000 g for 30 minutes (Beckman centrifuge, 20,000 rpm). The supernatant was discarded. The residue was resuspended in 0.75 ml of a glycine-NaCl buffer (0.1 mol of glycine, 0.17 mol of NaCl,0.5% (w:w) of eicosaoxyethylene sorbitan laurate (Tween ® 20), pH 8.2).

The mixture was then subjected to ultrasonic treatment (Bronson Sonyfier B 15) for 2 seconds. The reagent redispersed in this way was diluted with the abovementioned glycine-NaCl buffer in a volume ratio of 1:80 and treated with ultrasound again for 30 seconds.

4. Measurement of CRP concentrations in serum samples

The reagent for determination of CRP which was prepared according to Example 3 by binding anti-CRP antibodies to latex preparations according to the invention was used to measure CRP in patient sera. The LN-CRP standard (human) (Behringwerke AG) was used as the standard. According to the pack leaflet, this CRP standard contained 86 mg/liter of CRP. The standard was first diluted to 2.3 mg/liter in glycine-sodium chloride buffer (0.1 mol of glycine, 0.17M NaCl, pH 8.2) and then further diluted stepwise to twice the volume each time. A standard series of decreasing CRP concentrations was thus obtained. For measurement, 10 μl of standard serum dilution were mixed with 150 μl of a reactive buffer (0.1 mol of glycine, 0.17 mol of NaCl, 4% (w:w) of polyethylene glycol (PEG) 6000,0.5% (w:W) of eicosaoxyethylene sorbitan laurate (Tween ® 20), pH 8.2) and 50 μl of the reagent according to Example 3 in BLN cells (Behringwerke AG) and the mixture was incubated at room temperature for 30 minutes. The cells were then measured in a laser nephelometer (Behringwerke AG). The reference curve for measurement of the standard sera was plotted on semi-logarithmic paper and the measured values for the patient sera were evaluated on this curve. A typical reference curve is shown in FIG. 2.

I claim:

1. A process for the preparation of a dispersion polymer, which comprises the steps of first preparing a latex of a non-film-forming seed polymer having an incompletely polymerized monomer content of 5 to 50% by weight by carrying out the polymerization so that only 30% to 90% of the monomer present is polymerized completely, subsequently separating off the monomers not bonded to the polymer and then polymerizing a monomer mixture which contains at least one compound of the formula I containing acetal groups

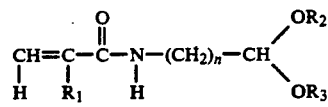

wherein n is 1—6;
R$_1$ is H or CH$_3$; and
R$_2$ and R$_3$ are identical or different, where
R$_2$ and R$_3$ are (CH$_2$)$_m$—CH$_3$, and m is 0—7, or

in which X, Y and Z are (CH$_2$)$_p$—CH$_3$ and P is 1—3, where X, Y and Z are identical or different, or R$_2$ and R$_3$ are an aryl radical,
and, in addition, up to 30% by weight, based on the mixture, of monomrs selected from acrylic acid, methacrylic acid, crotonic acid and mixtures thereof, and a further up to 30% by weight, again based on the total mixture, of carbocyclic aromatic vinylidene monomers in the presence of the seed polymer thus obtained.

2. A process for the preparation of a dispersion polymer as recited in claim 1, wherein said non-film-forming seed polymer is polystyrene and said carbocyclic aromatic vinylidene monomer is styrene.

3. A process for the preparation of a dispersion polymer as recited in claim 1, wherein said non-film-forming seed polymer is comprised of polymerized carbocyclic aromatic monovinylidene monomers.

4. A process for the preparation of a dispersion polymer as recited in claim 3, wherein said carbocyclic aromatic monovinylidene monomers are selected from the group consisting of styrene, vinyltoluene, vinylnaphthalene and mixture thereof.

5. A process for the preparation of a dispersion polymer as recited in claim 4, wherein said non-film-forming seed polymer has a particle diameter in the range of from about 0.05 to 0.5 μm.

6. A process for the preparation of a dispersion polymer as recited in claim 4, wherein said non-film-forming seed polymer, has an incompletely polymerized monomer content of about 20 to 30% by weight.

7. A process for the preparation of a dispersion polymer as recited in claim 6, wherein said non-film-forming seed polymer is formed by carrying out the polymerization so that only about 50 to 70% of the monomer present is polymerized completely.

8. A process for the preparation of a dispersion polymer as recited in claim 4, wherein said compound of the formula I is selected from the group consisting of an acryl- or methacrylamidoalkylaldehyde di-alkyl acetal having alkyl groups of from 2 to 8 carbon atoms.

9. A process for the preparation of a dispersion polymer as recited in claim 7, wherein said compound of the formula I is selected from the group consisting of an acryl- or methacrylamidoacetaldehyde di-n-pentyl acetal.

10. A process for the preparation of a dispersion polymer as recited in claim 9, wherein said monomer mixture containing at least one compound of the formula I is added dropwise to the latex of non-film-forming seed polymer which is heated to a temperature of from about 50° C. to 120° C.

11. A process for the diagnostic detection of antigens, antibodies or haptens in a sample which comprises:
 (a) incubating said sample with a biologically active dispersion polymer comprising biologically active agents, selected from antigens, antibodies or haptens which will bind with the antigen, antibody or hapten to be detected, bonded to a dispersion polymer which contains latex particles having an incompletely polymerized monomer content of 5 to 50% by weight, based on the latex particles, having on the surface of said latex particles a copolymer of a monomer mixture which contains at least one of the compounds of the formula I containing acetal groups

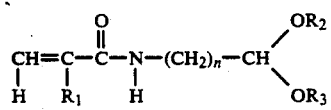

wherein
 n is 1—6;
 $R_1$ is H or $CH_3$; and
 $R_2$ and $R_3$ are identical or different, where
 $R_2$ and $R_3$ are $(CH_2)_m$—$CH_3$, and m is 0—7, or

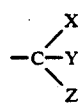

in which X, Y and Z are $(CH_2)_p$—$CH_3$ and P is 1—3, where X, Y and Z are identical or different, or $R_2$ and $R_3$ are an aryl radical; and
 (b) subjecting said biologically active dispersion polymer incubated with said sample to a means for detecting said antigen, antibody or hapten to be detected.

12. A process for the diagnostic detection of antigens, antibodies or haptens as recited in claim 11 wherein said means for detecting said antigen, antibody or hapten to be detected is selected from a nephelometric, turbidometric or particle counting method.

13. A process for the preparation of a biologically active dispersion polymer comprising the steps of:
 (1) preparing a latex of non-film-forming seed polymer having an incompletely polymerized monomer content of from about 5 to 50% by weight;
 (2) polymerizing in the presence of the seed polymer a monomer mixture which contains at least one compound of the formula I containing acetal groups

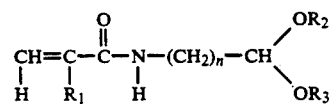

wherein n is 1—6;
 $R_1$ is H or $CH_3$; and
 $R_2$ and $R_3$ are identical or different, where $R_2$ and $R_3$ are $(CH_2)_m$—$CH_3$, and m is 0—7, or

in which X, Y and Z are $(CH_2)_p$—$CH_3$ and P is 1—3, where X, Y and Z are identical or different, or $R_2$ and $R_3$ are an aryl radical,
 and, in addition, up to 30% by weight, based on the mixture, of monomers selected from acrylic acid, methacrylic acid, crotonic acid and mixtures thereof, and a further up to 30% by weight, again based on the total mixture, of carbocyclic aromatic vinylidene monomers;
 (3) adjusting the pH of the resulting polymer latex to a pH of less than about 5; and
 (4) incubating the resultant polymer latex with the biologically active material to be bound thereto in the presence of a reducing agent.

14. A process for the preparation of a biologically active dispersion polymer as recited in claim 13, wherein said reducing agent comprises a solution of sodium cyanoborohydride in a neutral buffer.

15. A process for the preparation of a biologically active dispersion polymer as recited in claim 14, wherein said biologically active material is selected from the group consisting of antibodies, antigens and hapten.

16. A process for the preparation of a biologically active dispersion polymer as recited in claim 15, wherein said non-film-forming seed polymer is formed of polymerized monomers selected from the group consisting of styrene, vinyltoluene and vinylnaphthalene, and said compound of the formula I is selected from the group consisting of an acryl- or methacrylamidoacetaldehyde di-n-pentyl acetal.

* * * * *

UNITED STATES PATENT AND TRADEMARK OFFICE
CERTIFICATE OF CORRECTION

PATENT NO. : 5,183,766
DATED : FEBRUARY 2, 1993
INVENTOR(S) : WOLFGANG KAPMEYER

It is certified that error appears in the above-identified patent and that said Letters Patent is hereby corrected as shown below:

On the Title Page, Item [57], line 3, "being" should read --are--.

Claim 1, column 8, line 51, "P" should read --p--; and line 55, "monomrs" should read --monomers--.

Claim 4, column 9, line 5, "mixture" should read --mixtures--.

Claim 11, column 10, line 1, "P" should read --p--;

Claim 13, column 10, line 38, "P" should read --p--.

Claim 15, column 10, line 59, "hapten" should read --haptens--.

Signed and Sealed this

Nineteenth Day of April, 1994

Attest:

BRUCE LEHMAN

*Attesting Officer*   Commissioner of Patents and Trademarks